United States Patent
Reber et al.

(10) Patent No.: US 10,166,335 B2
(45) Date of Patent: Jan. 1, 2019

(54) DRIVE ASSEMBLY FOR AN AUTOINJECTOR AND A METHOD OF ASSEMBLING AN AUTOINJECTOR

(75) Inventors: Dominic Charles Reber, Cambridge (GB); Congyi Huang, Cambridge (GB); Matthew Young, Cambridge (GB)

(73) Assignee: OVAL MEDICAL TECHNOLOGIES LIMITED, Cambridge (GB)

( * ) Notice: Subject to any disclaimer, the term of this patent is extended or adjusted under 35 U.S.C. 154(b) by 983 days.

(21) Appl. No.: 13/989,556

(22) PCT Filed: Dec. 1, 2011

(86) PCT No.: PCT/GB2011/052375
§ 371 (c)(1),
(2), (4) Date: Aug. 9, 2013

(87) PCT Pub. No.: WO2012/073032
PCT Pub. Date: Jun. 7, 2012

(65) Prior Publication Data
US 2013/0317480 A1 Nov. 28, 2013

(30) Foreign Application Priority Data
Dec. 2, 2010 (GB) .................................. 1020472.5

(51) Int. Cl.
*A61M 5/20* (2006.01)
*A61M 5/32* (2006.01)

(52) U.S. Cl.
CPC ......... *A61M 5/2033* (2013.01); *A61M 5/3204* (2013.01); *A61M 2005/2013* (2013.01); *A61M 2005/2073* (2013.01); *Y10T 29/53* (2015.01)

(58) Field of Classification Search
CPC .............. A61M 5/2033; A61M 5/3204; A61M 2005/2073; A61M 2005/2013;
(Continued)

(56) References Cited

U.S. PATENT DOCUMENTS 7,806,866 B2 * 10/2010 Hommann .......... A61M 5/2033
604/136
2002/0004648 A1 * 1/2002 Larsen .................. A61M 5/326
604/195
(Continued)

FOREIGN PATENT DOCUMENTS

CN 1849148 A 10/2006
CN 101454032 6/2009
(Continued)

OTHER PUBLICATIONS

International Preliminary Report on Patentability from corresponding PCT/GB2011/052375 dated Jun. 13, 2013.
(Continued)

*Primary Examiner* — Jenna Zhang
(74) *Attorney, Agent, or Firm* — Lando & Anastasi, LLP

(57) ABSTRACT

The invention provides a drive mechanism for an autoinjector, configured to be coupled to a drug containing portion to form a complete autoinjector, the drive mechanism comprising: a housing (20); a drive means coupled to the housing, the drive means comprising a resilient member (22); a retaining means coupled to the housing, the retaining means (60) engaging the drive means in a first position to retain the resilient member in a deformed condition, and releasing the drive means in a second position; and a coupling means (24) for coupling with a drug containing portion (10). The drug containing portion retains the drive means in a second deformed condition when the retaining means is in the second position, the drive means storing enough energy in the second deformed condition to drive needle insertion and/or drug delivery.

16 Claims, 18 Drawing Sheets

(58) Field of Classification Search
CPC .. A61M 2005/3276; A61M 2005/3263; A61M 5/326; Y10T 29/53
See application file for complete search history.

(56) References Cited

U.S. PATENT DOCUMENTS

| | | | | |
|---|---|---|---|---|
| 2003/0105430 A1* | 6/2003 | Lavi | ................... | A61M 5/2033 604/136 |
| 2003/0120209 A1* | 6/2003 | Jensen | ................. | A61M 5/326 604/110 |
| 2004/0039336 A1* | 2/2004 | Amark | ................ | A61M 5/2033 604/136 |
| 2007/0129674 A1* | 6/2007 | Liversidge | ............ | A61M 5/326 604/110 |
| 2008/0195056 A1* | 8/2008 | Bishop | ................ | A61M 5/2033 604/218 |
| 2008/0228143 A1* | 9/2008 | Stamp | ................ | A61M 5/2033 604/157 |
| 2009/0270804 A1* | 10/2009 | Mesa | ................. | A61M 5/2033 604/111 |
| 2011/0118667 A1* | 5/2011 | Zaiken | ............... | A61M 5/3202 604/138 |
| 2011/0288491 A1* | 11/2011 | Newman | ............... | A61M 5/326 604/198 |

FOREIGN PATENT DOCUMENTS

| | | | |
|---|---|---|---|
| JP | 2005525879 | A | 9/2005 |
| JP | 2006507103 | A | 3/2006 |
| JP | 2007518507 | A | 7/2007 |
| JP | 2008508950 | A | 3/2008 |
| JP | 2009533124 | A | 9/2009 |
| JP | 2012504008 | A | 2/2012 |
| WO | 2003097133 | A1 | 11/2003 |
| WO | 2004047890 | A1 | 6/2004 |
| WO | 2005070481 | A1 | 8/2005 |
| WO | 2009103251 | A1 | 8/2009 |
| WO | 2009114542 | A1 | 9/2009 |
| WO | 2010035059 | A1 | 4/2010 |

OTHER PUBLICATIONS

English Translation of Chinese Office Action from corresponding Chinese Application No. 201180064512.9 dated Nov. 4, 2014.
English Translation of Chinese Office Action from corresponding Chinese Application No. 201180064512.9 dated Aug. 26, 2015.
English Translation of Notice of Reasons for Rejection from corresponding Japanese Application No. 2013-541427 dated Nov. 17, 2015.
English Translation of Second Notice of Reasons for Rejection from corresponding Japanese Application No. 2013-541427 dated Aug. 2, 2016.
Notification of Decision to Grant from corresponding Japanese Application No. 2013-541427 dated Apr. 26, 2017 (No English Translation available).
Notification of Grant from corresponding Chinese Application No. 201180064512.9 dated Apr. 7, 2016 (No English Translation available).

* cited by examiner

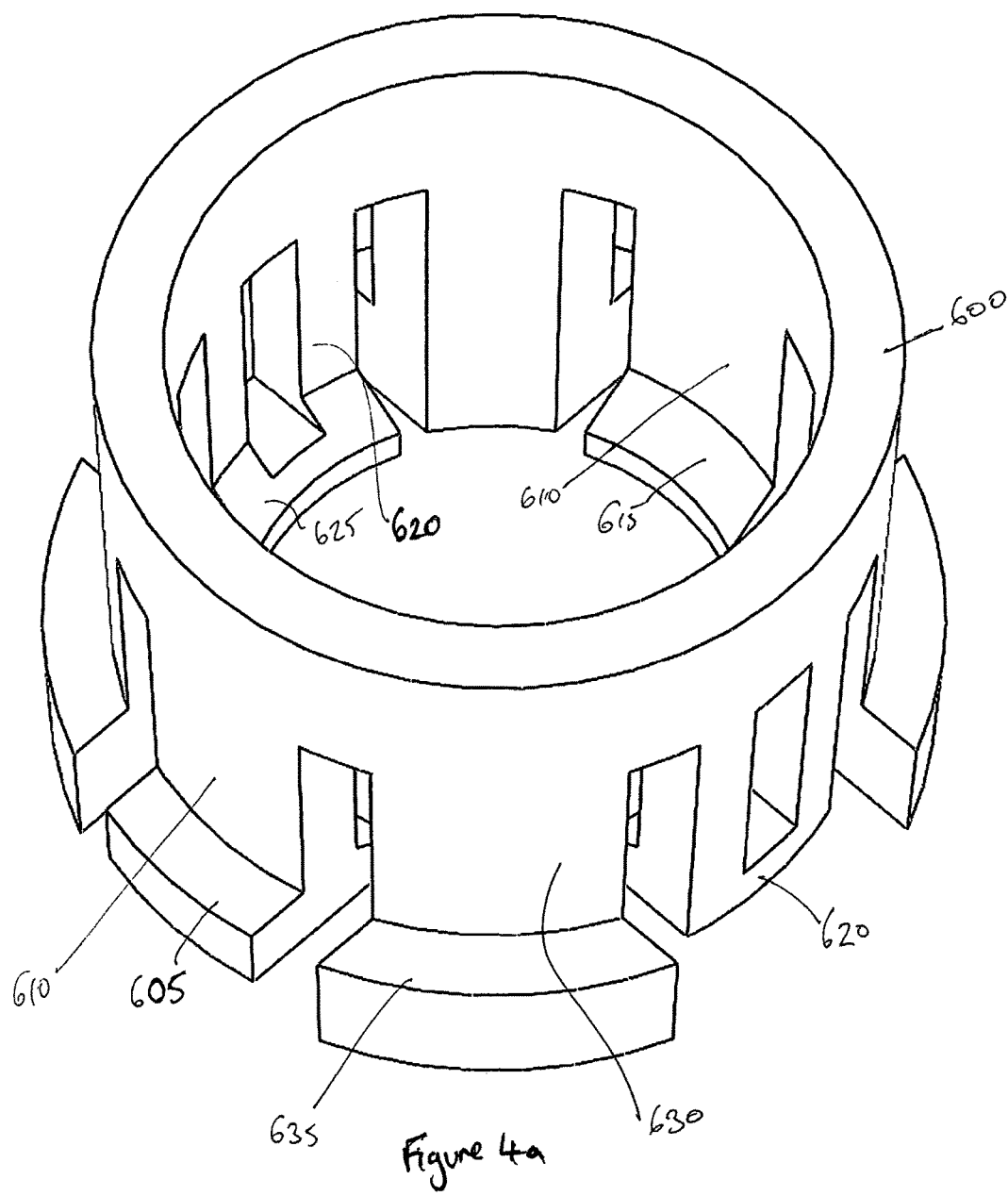

DRIVE ASSEMBLY FOR AN AUTOINJECTOR AND A METHOD OF ASSEMBLING AN AUTOINJECTOR

FIELD OF THE INVENTION

The present invention relates to autoinjectors and in particular to a drive assembly for an autoinjector that permits for simple assembly of an autoinjector.

BACKGROUND TO THE INVENTION

An autoinjector is a drug delivery device which contains a medical, therapeutic, diagnostic, pharmaceutical or cosmetic compound (drug) before it is administered, and which is used to administer the compound through the skin of the patient via a hollow needle. Autoinjectors may be used by the patient themselves or by a different user, and are also used to administer drugs to animals.

Autoinjectors are typically used because they reduce the amount of training and effort needed by a user compared with that needed for a syringe, by automating either or both processes of inserting the needle into the patient and expelling the drug through the needle. They can also reduce the fear of injection by hiding the needle from the patient Autoinjectors typically include a housing containing a drug and a plunger that is driven by an automatic mechanism to move the plunger within the housing to eject the drug. The automatic mechanism may also move the needle relative to the housing to insert the needle into a subject. Motive power for the mechanism may come from one or more springs or other power sources such as compressed gas.

Autoinjectors are used to deliver so-called crisis drugs such as epinephrine, where a patient may need to self-inject the drug while under the severe stress of anaphylactic shock. They are also used to deliver drugs for long-term conditions such as rheumatoid arthritis, where the patient may have limited dexterity. In both cases it is beneficial for the autoinjector to have a simple and easy user interface in order to maximise the likelihood that the patient is able to operate the autoinjector correctly and receive the drug. Some autoinjectors include a finger-operated button or other control to allow the patient to activate them, but this approach can be confusing and more difficult to use. Other autoinjectors advantageously incorporate a very simple user interface design where the autoinjector is activated and the drug delivered by the action of the patient pressing a skin sensor component against the injection site.

Autoinjectors typically have a housing which encloses a needle at the front end close to the injection site, a drug container, and one or more drive members such as springs towards the back of the device at the other end from the injection site. Typically an autoinjector is manufactured as partial subassemblies by a specialist device manufacturer, and these partial subassemblies are then assembled with a filled drug container at another site, often the filling facility for the drug container, to form the complete autoinjector. The device manufacturers are generally not able to handle the drug component. Equally, the filling facilities generally lack device assembly expertise or capability. For this reason it is advantageous to be able to safely transfer autoinjector subassemblies from the device manufacturer to the final assembly facility, and then assemble them with the filled drug container with minimum assembly operations and manufacturing complexity.

In order to allow the drug container to be assembled into the final autoinjector, autoinjectors are typically shipped to the final assembly location as two subassemblies, a front subassembly including a skin sensor if incorporated into the design, and a rear subassembly including the power source in an energised condition, and a button if incorporated into the design. This requires the rear subassembly to contain the stored energy source safely before final assembly, without releasing the energy prematurely.

Autoinjectors with activation buttons positioned on the rear subassembly of the autoinjector typically rely on this button to retain the stored energy source safely before final assembly. However if the design of the autoinjector is such that the autoinjector is activated only by the action of the patient pressing a skin sensor at the front end of the autoinjector onto the injection site, without the use of a separate finger-operated button, then there is a requirement for the rear subassembly to contain the stored energy source safely before final assembly, but to allow it to be released when needed during activation of the skin sensor which is in the front subassembly. This can be difficult and complex to achieve, and can increase the size and cost of the autoinjector. There is a risk that energy source can be released before final assembly due to handling forces.

It is an object of the present invention to provide a drive mechanism for an autoinjector that can be safely shipped in locked state, in which it cannot be activated, but which can be simply assembled to another component or components to form an autoinjector, in which the drive mechanism can be simply activated.

SUMMARY OF THE INVENTION

Aspects of the present invention are defined in the appended independent claims, to which reference should be made. The various aspects of the invention may be provided alone or in combination with one or more of the other aspects. Preferred features of the invention are defined in the dependent claims.

The present invention relates to a system and method of assembling an autoinjector. In particular it relates to a drive mechanism for an autoinjector that can be assembled separately to a drug containing portion of the autoinjector and coupled to the drug containing portion as a final step in the manufacture of the autoinjector and changed from a first locked state, in which the drive mechanism cannot be activated, to a second unlocked state, in which the drive mechanism can be activated to cause a drug to be delivered to a patient from the drug containing portion. The change to the second unlocked state is advantageously carried out before the autoinjector reaches the end user or patient.

In a first aspect the invention provides a drive mechanism for an autoinjector, configured to be coupled to a drug containing portion to form a complete autoinjector, the drive mechanism comprising:
　a housing;
　a drive means coupled to, or forming part of, the housing, the drive means comprising a resilient member;
　a retaining means coupled to, or forming part of, the housing, the retaining means engaging the drive means in a first position to retain the resilient member in a first deformed condition, and releasing the drive means when moved to a second position; and
　a coupling means for coupling with a drug containing portion, such that the drug containing portion retains the drive means in a second deformed condition when the retaining means is moved to the second position, wherein the drive means in the second deformed condition stores sufficient potential energy for driving the autoinjector.

The retaining means may comprise a locking component, the locking component engaging one or more apertures or locking surfaces on the housing in the first position: The locking component may be disengaged from the one or more apertures or locking surfaces on the housing in the second position. Alternatively, or in addition, the locking component may be disengaged from the drive means in the second position.

Alternatively, the locking component may be formed integrally with the housing and so form part of the housing at least in the first position. The resilient member may also be integral with the housing.

The resilient member may comprise one or more deformable springs held within the housing. The drive means may further comprise a spring engaging component, the spring engaging component coupled to the resilient member and to the retaining means in the first position. The spring engaging component may form a pusher rod in an assembled autoinjector.

The spring engaging component may have a first bearing surface and the locking component may have a second bearing surface, wherein, in the first position, the first bearing surface engages the second bearing surface.

The locking component may be resilient and may be stressed in the second position. Alternatively the locking component may be stressed in the first position and so biased into contact with a bearing surface or aperture on the housing or on the drive means. In this way the locking component is biased to retain the drive means in the first position and it requires a positive action on the locking component to release it from engagement with the housing or drive means. Preferably, the locking component engages a plurality of apertures in the housing. The apertures may be configured so that a specially adapted tool is required to move the locking component out of engagement with all of the apertures simultaneously to release the drive means.

When the drive mechanism is coupled to a front end component to form an autoinjector, the drive means is retained in a second deformed state in the second position. The drive means is preferably retained in the second deformed state by the front end component and still stores sufficient potential energy for needle insertion and/or drug ejection when the autoinjector is to be used.

The retaining means may be connected to the coupling means such that the retaining means cannot move to the second position when the coupling means is not engaged with a drug containing portion. Once the drive mechanism is coupled to the drug containing portion, the retaining means can be moved to the second position. This provides for additional security during transit. For example, the coupling means may include a element that moves during coupling to expose an aperture in which the retaining means is engaged, exposure of the aperture allowing a tool to be used to disengage the retaining means.

The coupling means is preferably provided on the housing and may be a latch, aperture, screw fitting or any other suitable means to engage with a front end component of an autoinjector.

In a second aspect the invention provides an autoinjector comprising a drive mechanism in accordance with the first aspect. Preferably, the autoinjector further comprises a front end portion, the front end portion retaining the drive means in a second deformed condition when the retaining means is in the second position. The front end portion preferably comprises a release mechanism to release the drive means from the second deformed condition to deliver a drug. The release mechanism preferably comprises a movable skin sensor, configured such that when the skin sensor is pressed onto an injection site, the skin sensor moves to release the drive means from the second deformed condition.

Preferably, the autoinjector comprises a drug container containing a drug to be dispensed and a plunger. The retaining means, or the spring engaging component, or both, may form a pusher rod configured to engage the plunger during operation of the autoinjector.

In a third aspect, the invention provides a method of assembling an autoinjector comprising the steps of:
  assembling a drive mechanism containing an energised resilient drive member in a first retained state;
  assembling the drive mechanism to a drug containing portion
  releasing the energised resilient drive member to a second retained state so that it can subsequently provide a drive means for delivering a drug.

In one embodiment, the invention provides a method for assembling an autoinjector comprising the steps of:
  placing a resilient drive member in a first housing portion;
  retaining the resilient drive member in the housing in a first deformed condition using a retaining means coupled to the drive member and the first housing portion in a first position;
  coupling the first housing portion to a second housing portion, the second housing portion containing a drug to be dispensed by the autoinjector;
  moving the retaining means to a second position to release the resilient drive member to second deformed condition, wherein in the second deformed condition the drive member stores sufficient potential energy to drive the autoinjector, e.g. for needle insertion and/or drug ejection when the autoinjector is to be used.

The step of moving the retaining means may be performed as a consequence of the step of coupling or may be performed as a separate action. If it is performed as a separate action it may be performed as a step in an automated assembly process.

The step of moving the retaining means may comprise pushing a portion or portions of the retaining means through one or more apertures in the first housing portion. Alternatively, the step of moving the retaining means may comprise removing a portion or portions of the retaining means from the first housing portion. Alternatively, or in addition, the step of moving the retaining means may comprise breaking a portion or portions of the retaining means, rotating one portion against another or otherwise altering their relative states or conditions.

In a fourth aspect, the invention provides a kit for assembly into an autoinjector, the kit comprising: a drive mechanism, and a drug containing portion, the drive mechanism comprising:
  a housing;
  a drive means coupled to, or forming part of, the housing, the drive means comprising a resilient member;
  a retaining means coupled to, or forming part of, the housing, the retaining means engaging the drive means in a first position to retain the resilient member in a first deformed condition, and releasing the drive means when moved to a second position; and
  a coupling means for coupling with a drug containing portion;
  wherein, when the drive means is coupled to the drug containing portion, the drug containing portion retains the drive means in a second deformed condition when the retaining means is moved to the second position, wherein the drive means in the second deformed condition stores sufficient potential energy for driving the autoinjector.

BRIEF DESCRIPTION OF THE DRAWINGS

Embodiments of the invention will now be described, by way of example only, with reference to the accompanying drawings, in which:

FIG. 1b is a perspective view of the autoinjector of FIG. 1a;

FIG. 2b shows a horizontal section through the FIG. 2a;

FIG. 2c shows a vertical section through the autoinjector of FIG. 2a;

FIG. 3a shows a horizontal section through the drive mechanism of the autoinjector of FIG. 2a;

FIG. 3b shows a vertical section through the drive mechanism of the autoinjector of FIG. 2a;

FIG. 4a is a perspective view of the locking component of FIG. 2a;

FIG. 4b is a different perspective view of the locking component of FIG. 2a;

FIG. 5 is a perspective view of the spring engaging component of FIG. 2a;

FIG. 6 shows a horizontal section through the drug container of FIG. 2a;

FIG. 7 shows a horizontal section through the front portion of the autoinjector of FIG. 2a;

DETAILED DESCRIPTION

Figure 1A:
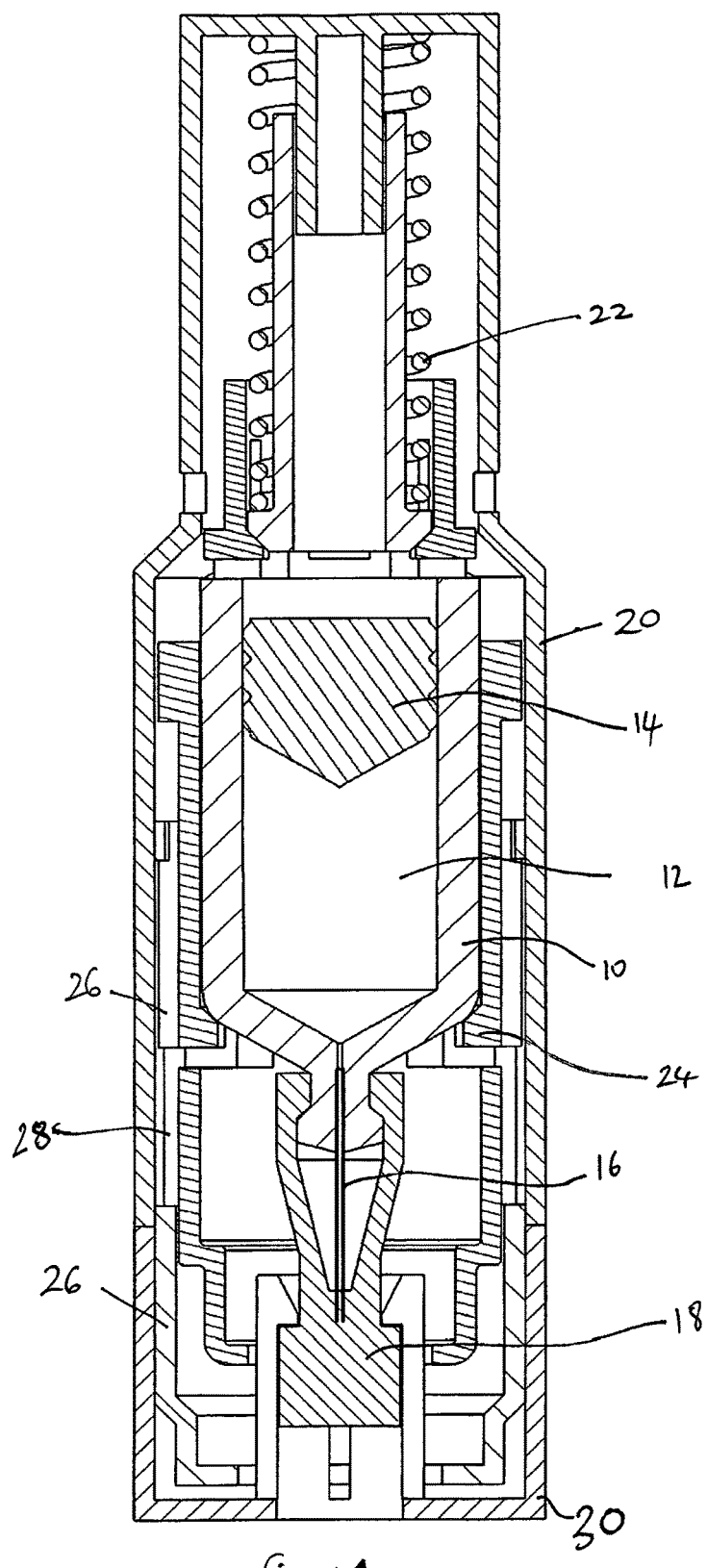
FIG. 1a is a cross sectional view of an assembled autoinjector in an unlocked state in accordance with the invention.

FIG. 1 is a cross section of an autoinjector in accordance with an embodiment of the invention. The autoinjector comprises a drug container 10 holding a drug 12. The drug container is closed by a plunger 14 at its rear end. In this embodiment, the drug container is formed from cyclic olefin copolymer, but it may be formed from any suitable plastics material or may be formed of glass. The plunger is formed from a rubber material, such as styrene butadiene rubber. At the front end of the drug container there is a hypodermic needle 16, which is fixed to the drug container 10 using an adhesive, or another suitable fixing mechanism. The front end of the needle 16 is embedded in a rubber sock 18, which is coupled to the drug container and completely seals the needle, keeping it sterile.

The drug container and needle assembly is held within an autoinjector housing 20. Also within the housing 20 is a drive mechanism comprising a stored energy source in the form of a helical spring 22 that is used to drive both insertion of the needle 16 into a patient and to move the plunger 14 within the drug container to expel the drug through the needle 16 into the patient. Any suitable deformable resilient member may be used as the stored energy source.

An activation mechanism is held within a front portion of the housing 20. Retaining arms 24 engage a front portion of the drug container against the action of the spring 22 to prevent activation of the autoinjector. A skin sensor component 26 is provided that extends around the retaining arms. When the skin sensor component 26 is moved backward relative to the retaining arms, the front ends of the retaining arms 24 can move into cut-out portions 28 in the skin sensor, releasing the drug container 10 to move forward through the housing 20. Operation of the autoinjector is described in more detail with reference to FIGS. 9 to 13.

A safety cap 30 is provided over the front end of the housing and skin sensor component 26, which engages the rubber sock 18. Removal of the safety cap also results in removal of the rubber sock. Activation of the autoinjector is not possible prior to removal of the safety cap 30.

Figure 1B:
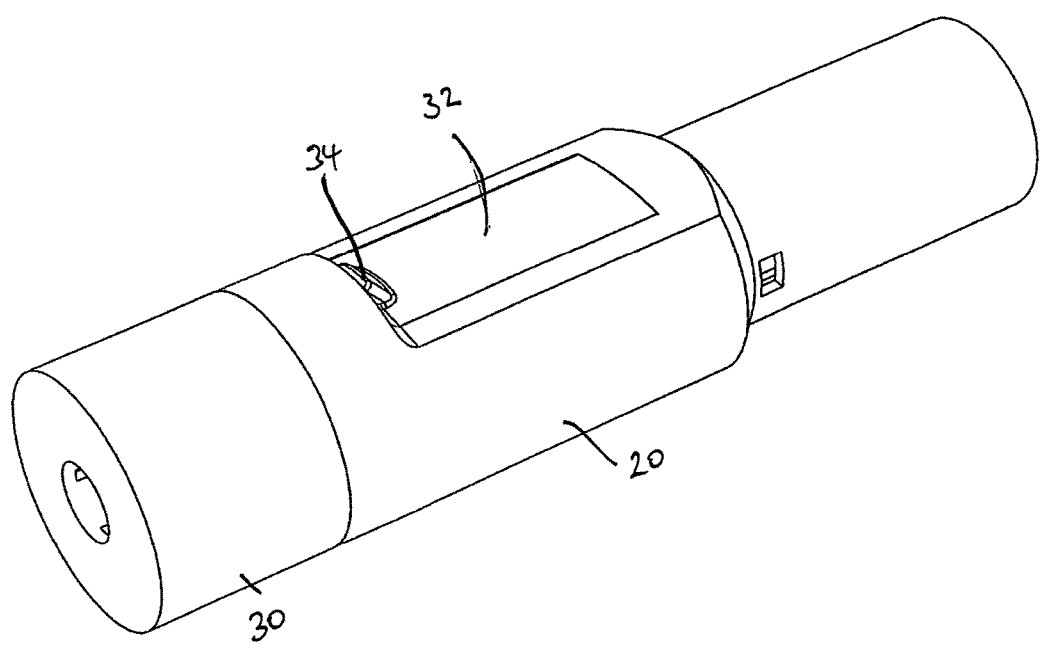

FIG. 1b is a perspective view of the autoinjector of FIG. 1a. It can be seen that the autoinjector has a generally round cross-section. The housing includes a window 32, through which the contents of the drug container can be viewed.

Figure 2A:
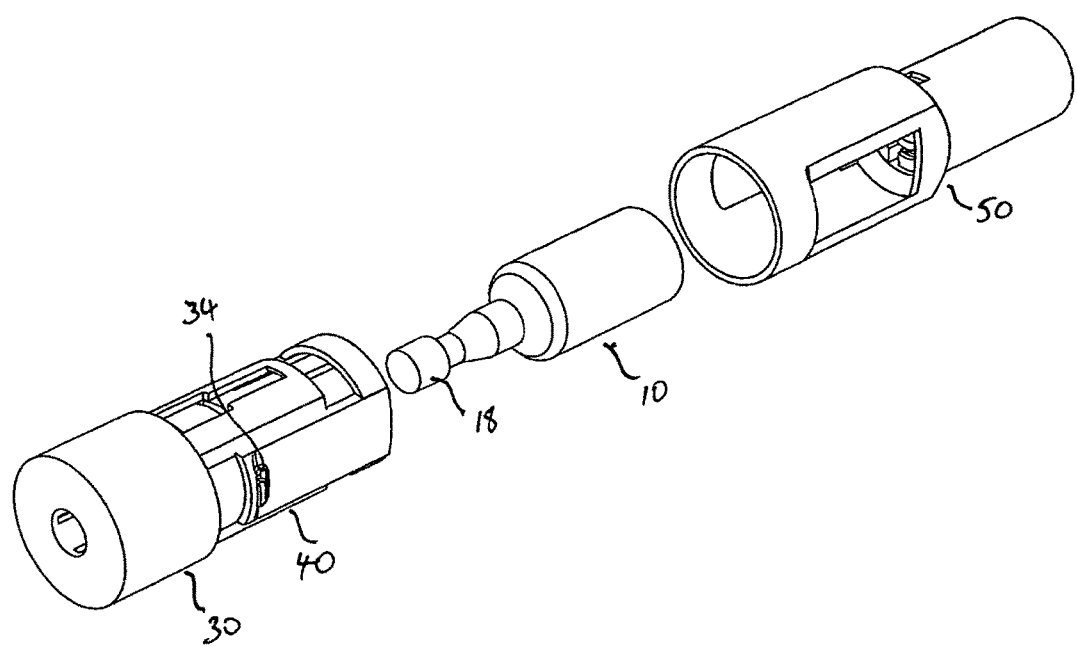
FIG. 2a is a perspective view of the autoinjector of FIG. 1 in disassembled form.
Figure 2B:
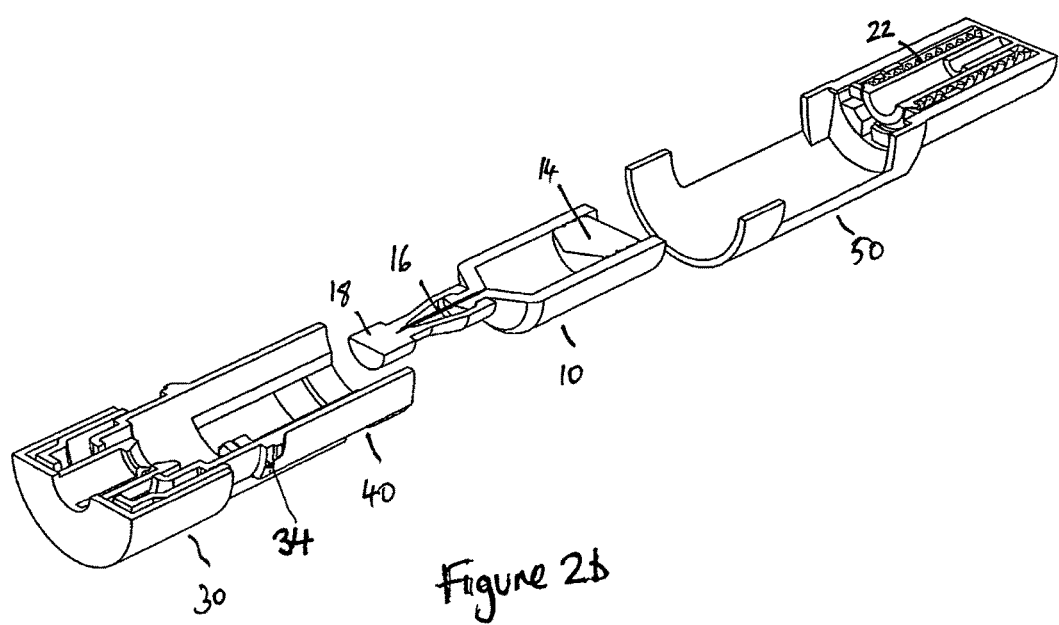
Figure 2C:
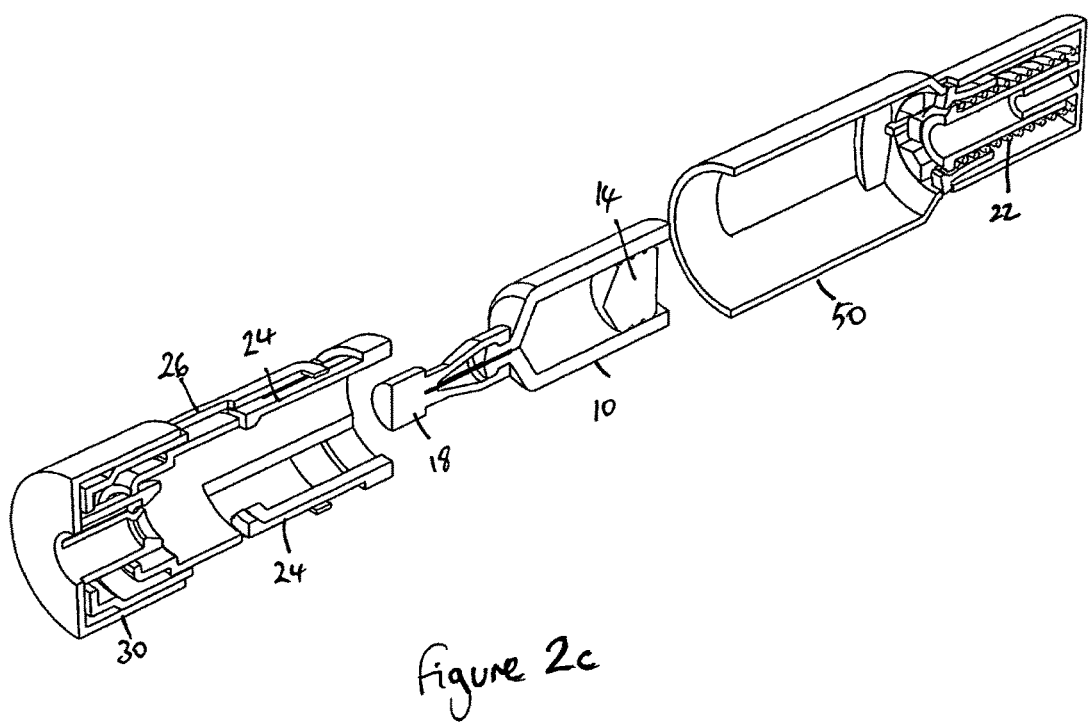

The autoinjector of FIGS. 1a and 1b is assembled from three initially separate parts: a front end portion 40, including the safety cap and activation mechanism, the drug container 10, including the plunger 14 and the rubber sock 18 for keeping the needle and drug in a sterile condition, and a rear portion 50 including the drive mechanism. FIG. 2a is a perspective view of these three separate parts in an unassembled state. FIG. 2b shows a horizontal section of FIG. 2a and FIG. 2c shows a vertical section of FIG. 2a. These separate parts are assembled together at a final stage of manufacture, after the drug container has been filled with the required drug.

Figure 3A:
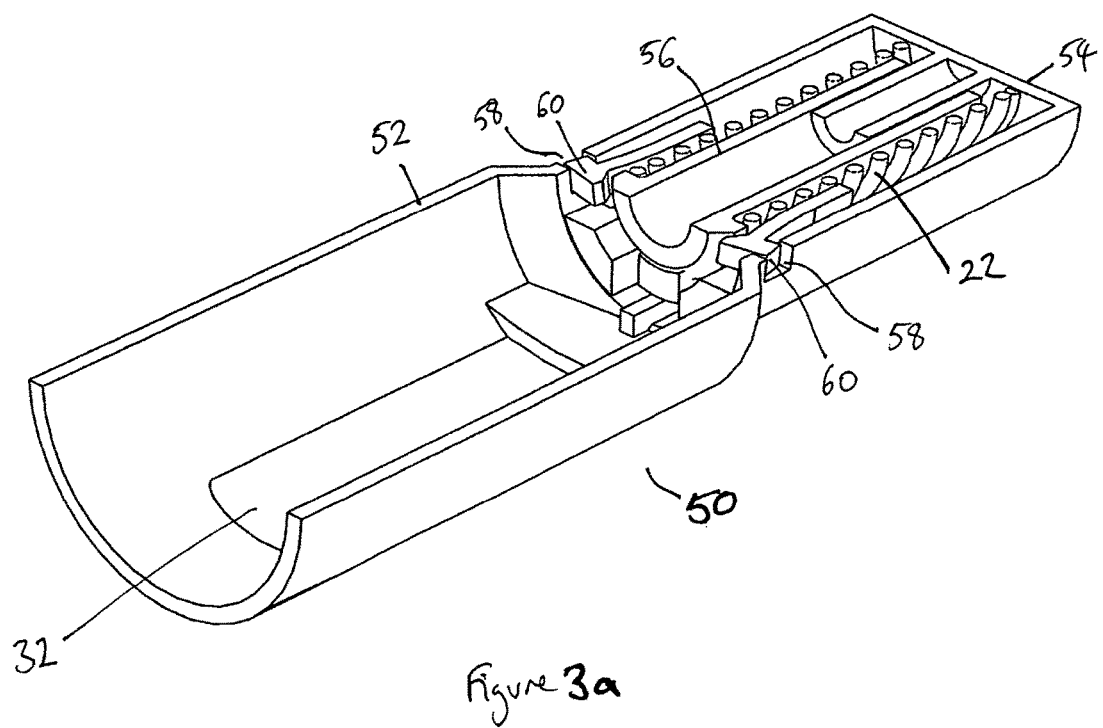
Figure 3B:
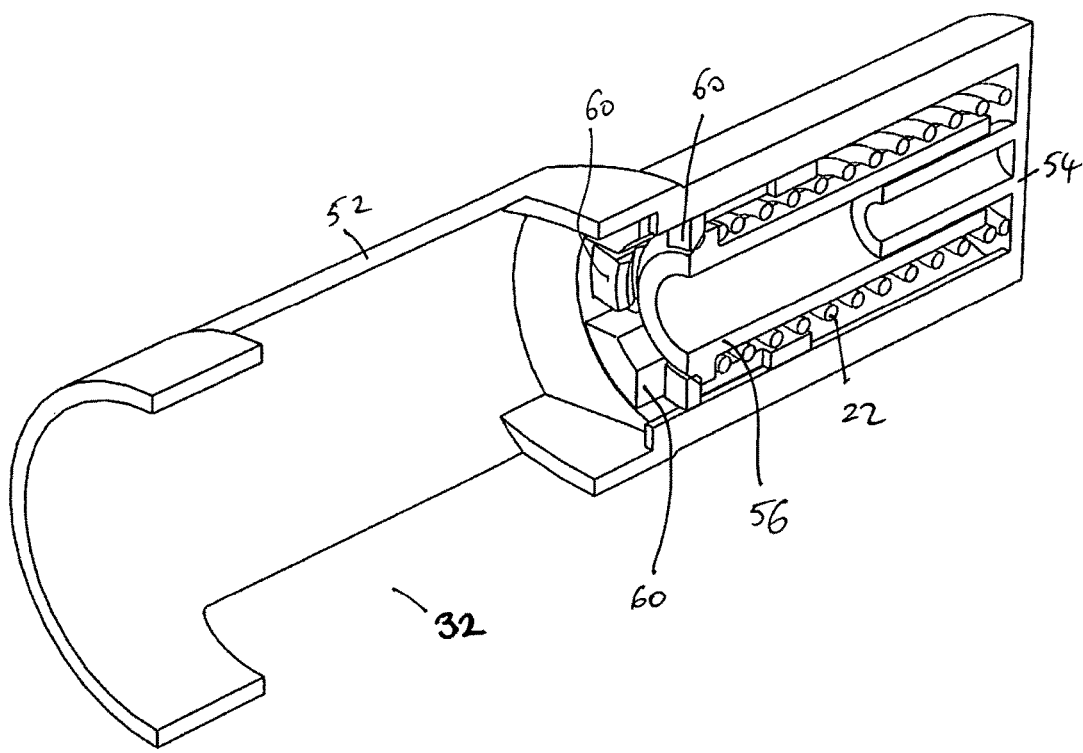
Figure 5:
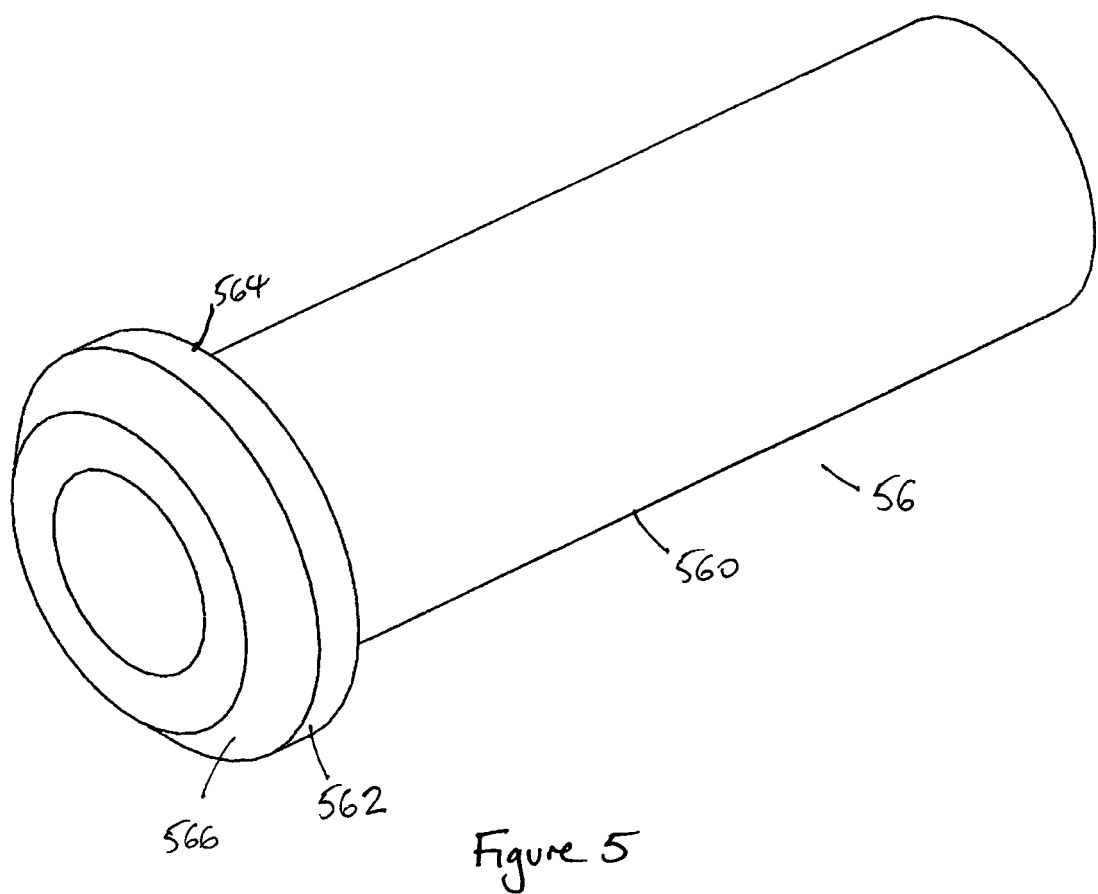

Each of the separate parts will now be described in more detail. FIG. 3a shows a horizontal section through the rear portion 50, with the spring in a first compressed condition and the locking component in the first position. FIG. 3b shows a corresponding vertical section through the rear portion. The rear portion includes a rear housing 52, which includes window 32. The rear housing 52 encases the drive mechanism. The drive mechanism comprises a spring 22 in a first deformed condition, in this example a compressed condition. The spring 22 is retained in the first compressed condition between the rear surface of the housing 54 and a spring engaging component 56. The spring engaging component 56 acts as a pusher in the assembled autoinjector, as described with reference to FIGS. 9 to 13. The spring engaging component 56 is shown in FIG. 5 and comprises a cylindrical portion 560 around which spring 22 sits, and a head portion 562 of larger diameter than the cylindrical portion 560. The head portion comprises a rear bearing surface 564 against which the front end of spring 22 is pressed, and a front bearing surface 566 which engages a locking component 60. The locking component 60 retains the spring engaging component and the spring 22 when in a first position. The front bearing surface 566 is chamfered or angled in the region that engages the locking component 60 to allow the spring engaging component 56 to slide past the locking component 60 during drug delivery, as will be described in detail with reference to FIG. 11.

The locking component 60 bears against the spring engaging component and against the housing 52. Specifically, in a first position the locking component engages two apertures formed in the housing 52. The locking component 60 is thereby locked in the first position against the action of the spring 22, retaining the spring 22 in a first deformed condition.

Figure 4B:
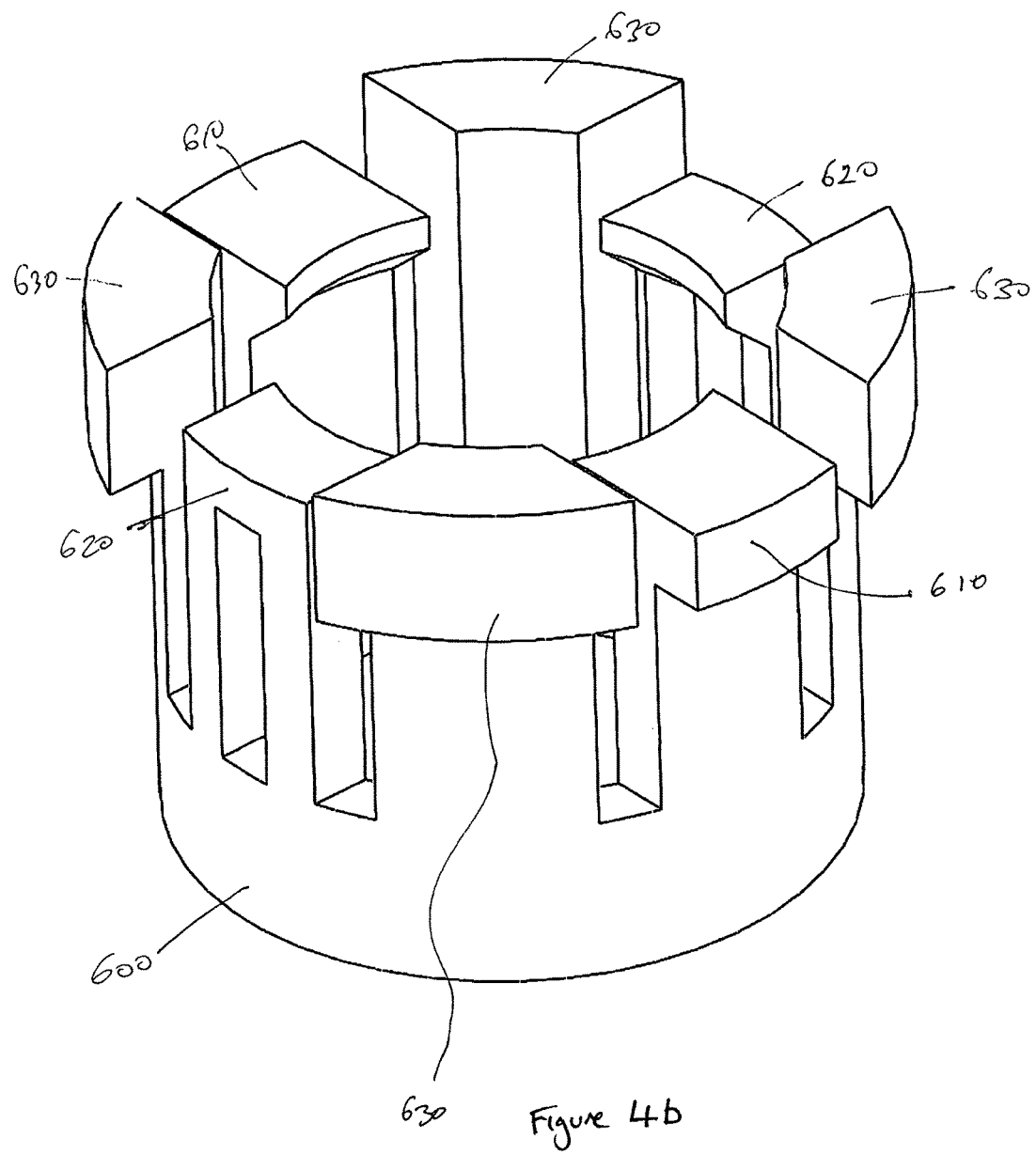
Figure 9:
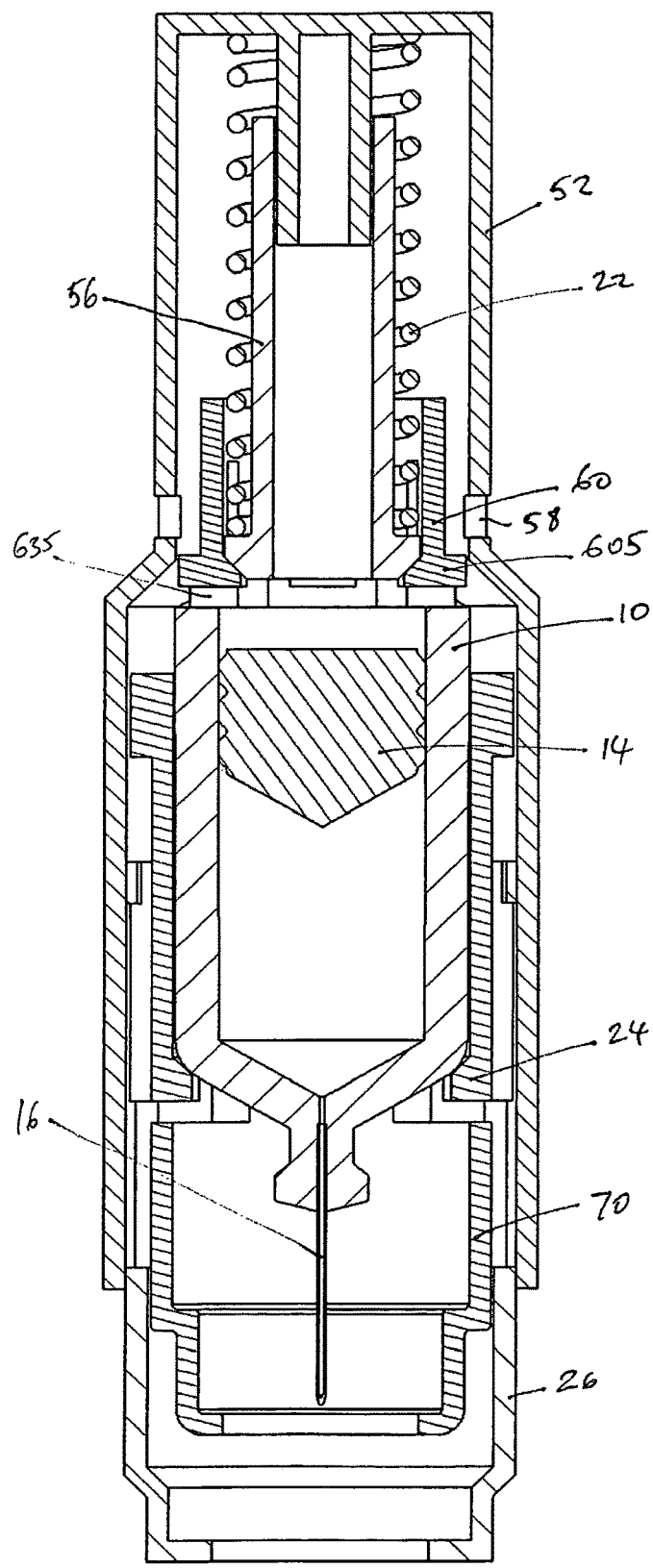
FIG. 9 is a section of the autoinjector of FIG. 1 with the safety cap removed.
Figure 11:
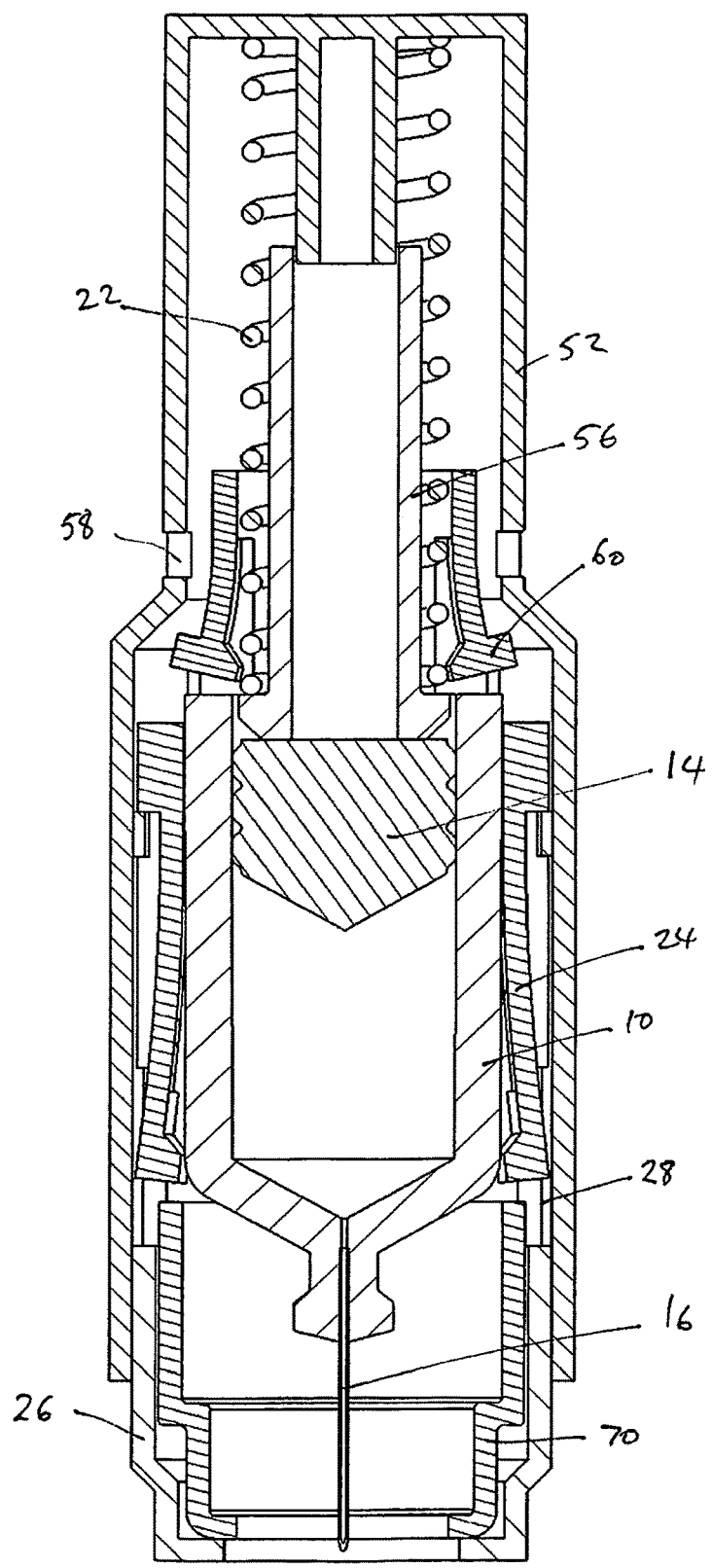
FIG. 11 is a section of the autoinjector of FIG. 1 with the drive means released from the second position.

The locking component 60 is shown separately in FIGS. 4*a* and 4*b*. The locking component is in the form of a collar having eight legs extending at their proximal ends from a ring section 600. Two resilient legs 610, diametrically opposite each other, have at their distal ends, inner bearing surfaces 615 extending radially inwards for engaging with the front bearing surface 566 of spring engaging component 56. A further two legs 620 also have inner bearing surfaces 625 at their distal ends extending radially inwards for engaging with the front bearing surface 566 of spring engaging component 56. The inner bearing surfaces 615, 625 are angled to match the angle of the front bearing surface 566. In this embodiment, the inner bearing surfaces are at an angle of about 45 degrees from the longitudinal axis of the spring engaging component. Legs 610 also have radially outwardly extending lugs 605 at their distal ends. Lugs 605 engage with apertures 58 in the rear housing 52. There are four further legs 630 that have no inner bearing surfaces but have radially outward extending lugs 635, which provide contact surfaces for the drug container when the spring 22 is in a second deformed condition, as shown in FIG. 9. The further legs 630 are longer than legs 610 and 620 to allow the legs 610 and 620 to deflect freely when further legs 630 are in contact with the drug container. This allows the spring engaging component to pass through the locking component without the legs 610 and 620 of the locking component jamming on the drug container, as shown in FIG. 11.

The locking component 60, spring engaging component 56 and housing 52 are all formed from a plastics material such as polyoxymethylene (POM) and may be formed by injection moulding.

Figure 6:
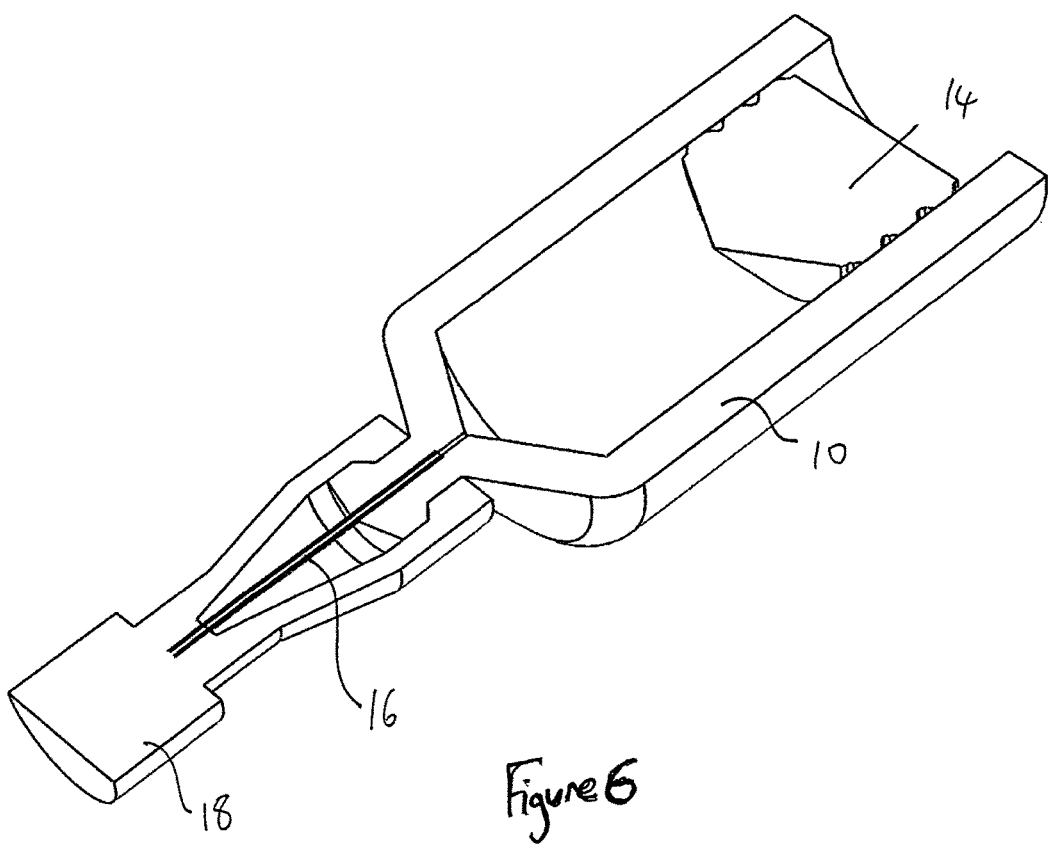

FIG. 6 shows a horizontal section through the drug container 10. As described with reference to FIG. 1, the drug container 10 is closed by a plunger 14 at its rear end. In this embodiment, the drug container is formed from cyclic olefin copolymer, but it may be formed from any suitable plastics material or may be formed of glass. The plunger is formed from a rubber material, such as styrene butadiene rubber. At the front end of the drug container a hypodermic needle 16 is fixed to the drug container 10 using an adhesive, or another suitable fixing mechanism. The front end of the needle 16 is embedded in a rubber sock 18, which is coupled to the drug container and completely seals the needle, keeping it sterile.

Figure 7:
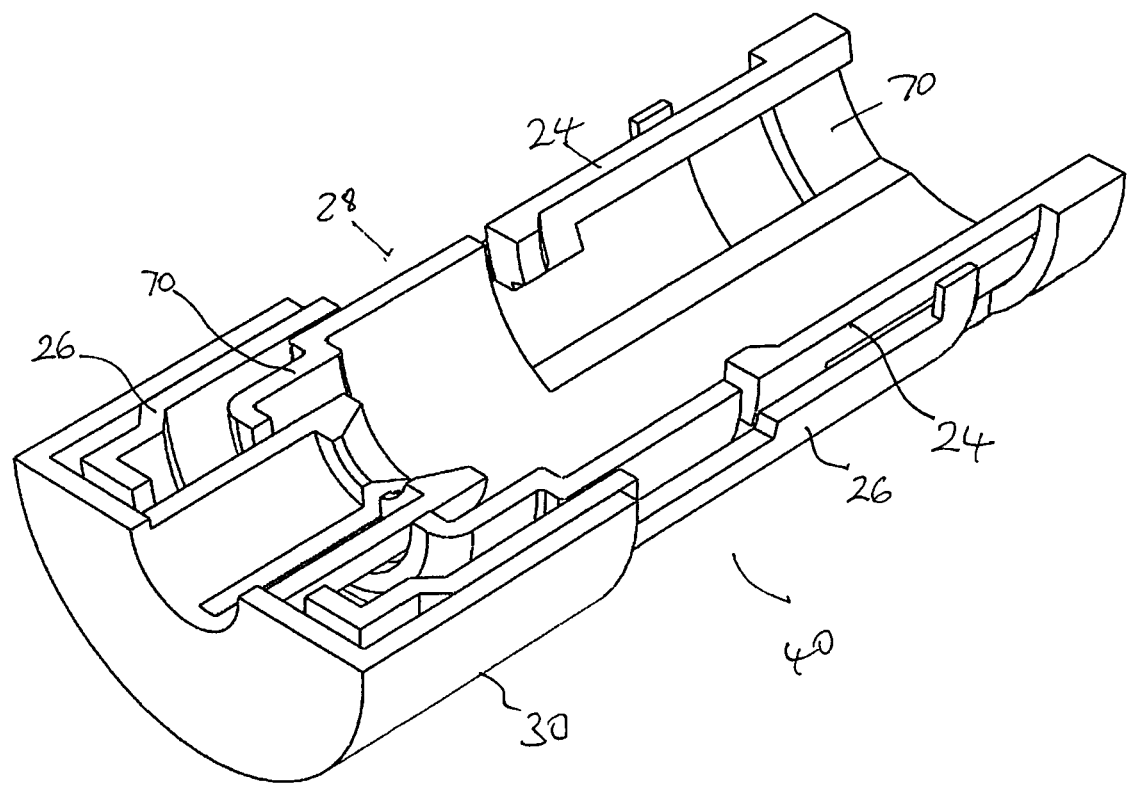

FIG. 7 shows a cross section through the front end portion 40. Front end portion includes safety cap 30, skin sensor component 26, and front end housing 70. Front end housing is configured to receive the drug container 10. Resilient arms 24, which are configured to engage the front end of the drug container 10, are formed as part of the front end housing 70. Skin sensor component 26 fits around, and is slidable on, the front end housing 70. Skin sensor component 26 includes window portions 28, into which the free ends of the resilient arms can be displaced when the skin sensor component is pushed back on front end housing 70. Skin sensor component 26 is retained on front end housing by the engagement of lugs on the front end housing (not shown) with a window (not shown) in the skin sensor component. Safety cap 30 cap be secured to the skin sensor component using any suitable mechanical fitting, such as a screw fitting or a push fitting. The front end housing, skin sensor component and safety cap are all formed from polyester thermoplastic in this example, but may be formed from any suitable plastics material.

Figure 8:
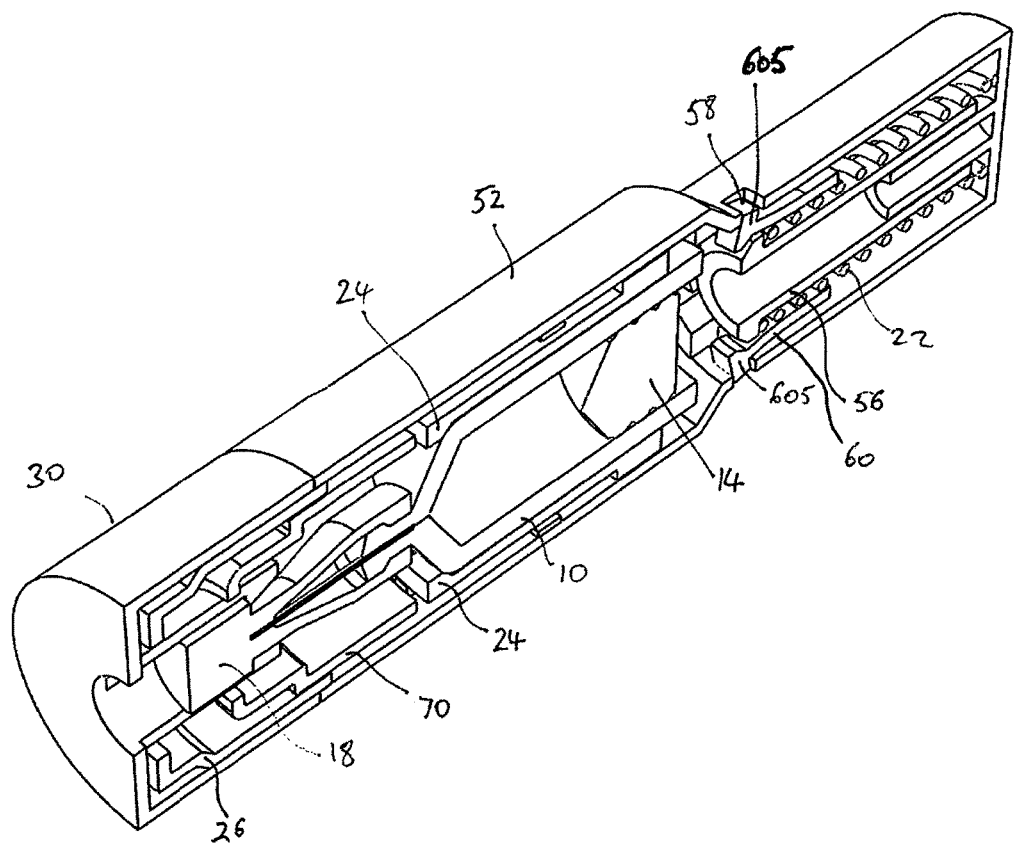
FIG. 8 shows a vertical section through an assembled autoinjector, in a locked state.

FIG. 8 shows a cross section of an autoinjector assembled from the components described with reference to FIGS. 2 to 7, in a locked state. The filled drug container 10 is received in the front end portion 40. The rubber sock 18 is pushed into the socket on the safety cap and received in a snap fitting so that subsequent removal of the safety cap 30 pulls the sock 18 off the needle. The rear portion 50 is fitted over the drug container 10 and the front end housing 70 and is coupled and secured to the front end housing by latches 34 shown in FIGS. 1*b*, 2*a* and 2*b*. Latches 34 engage with a front end of windows 32 in the rear portion housing 52. Any suitable coupling between the rear portion 50 and the front end portion 40 may be used. For example, a latch on the rear portion housing may be used to engage an aperture in the front end portion housing, or a screw fitting may be used.

FIG. 8 shows the autoinjector immediately after the three parts have been assembled to one other but before the autoinjector has been unlocked. The locking components 60 are still received in apertures 58 in the rear portion housing 52, retaining the spring 22 in a first deformed condition. In this condition the autoinjector cannot be activated by the skin sensor 26. In order to unlock the autoinjector the lugs 605 of the locking component 60 must be pushed inside the rear portion housing 52. The locking component legs are resilient so that both lugs 605 must be pushed inwards simultaneously to release the locking component and a specifically designed tool can be used to do this during an automated filling and assembly process. The requirement to push more than one lug simultaneously prevents accidental unlocking before the autoinjector has been assembled.

FIG. 9 shows a cross section of the autoinjector after it has been unlocked and with the safety cap 30 removed, but before use. The lugs 605 are disengaged from the apertures 58 and the spring 22 has therefore been released from the first deformed condition and has expanded. The spring is only allowed to expand a small amount and is retained in a second deformed condition by the abutment of the locking component 60 against the drug container 10. Specifically the lugs 635 on the locking component abut the rear end of the drug container 10. The drug container is prevented from forward movement by the resilient arms 24, which engage the front end of the drug container. The resilient arms are fixed relative to the rear portion housing 52 by the latches 34 engaging the windows 32, as shown in FIG. 1*b*. In this second deformed condition the spring 22 still stores enough energy for the needle insertion and drug ejection operations.

Figure 10:
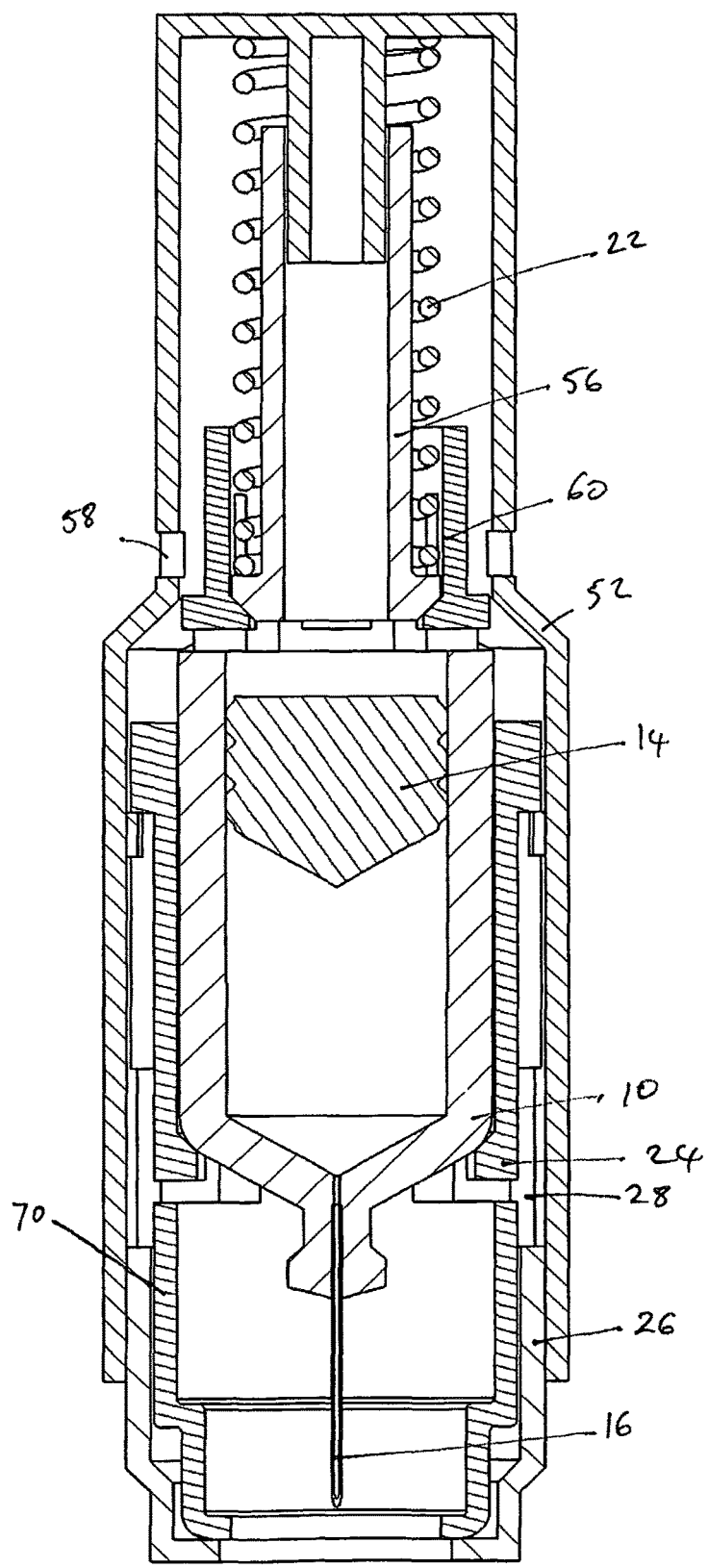
FIG. 10 is a section of the autoinjector of FIG. 1 with the skin sensor depressed.

FIGS. 10 to 13 show cross sections of the autoinjector at various stages during its use. FIG. 10 shows the autoinjector with the skin sensor component pushed back, as it would be when pressed against a patient's skin. The skin sensor component 26 is moved rearward until the windows 28 in the skin sensor component align with the ends of the resilient arms 24. At this point the spring 22 is still in the second deformed condition.

The force exerted by the spring 22 on the drug container 10 pushes the resilient arms outward into the windows 28 allowing the drug container 10 to move forward through the front end housing 70. This is shown in FIG. 11. The locking component is also moved forward into a region of the rear portion housing of increased diameter. This allows the legs of the locking component 60 to flex outwardly and the spring engaging component 56 to disengage from and move through the locking component 60. The spring engaging component then contacts the plunger 14 and acts as a pusher to drive both the drug container forward to insert the needle into a patient and to move the plunger 14 through drug container 10 to expel the drug through the needle 16.

Figure 12:
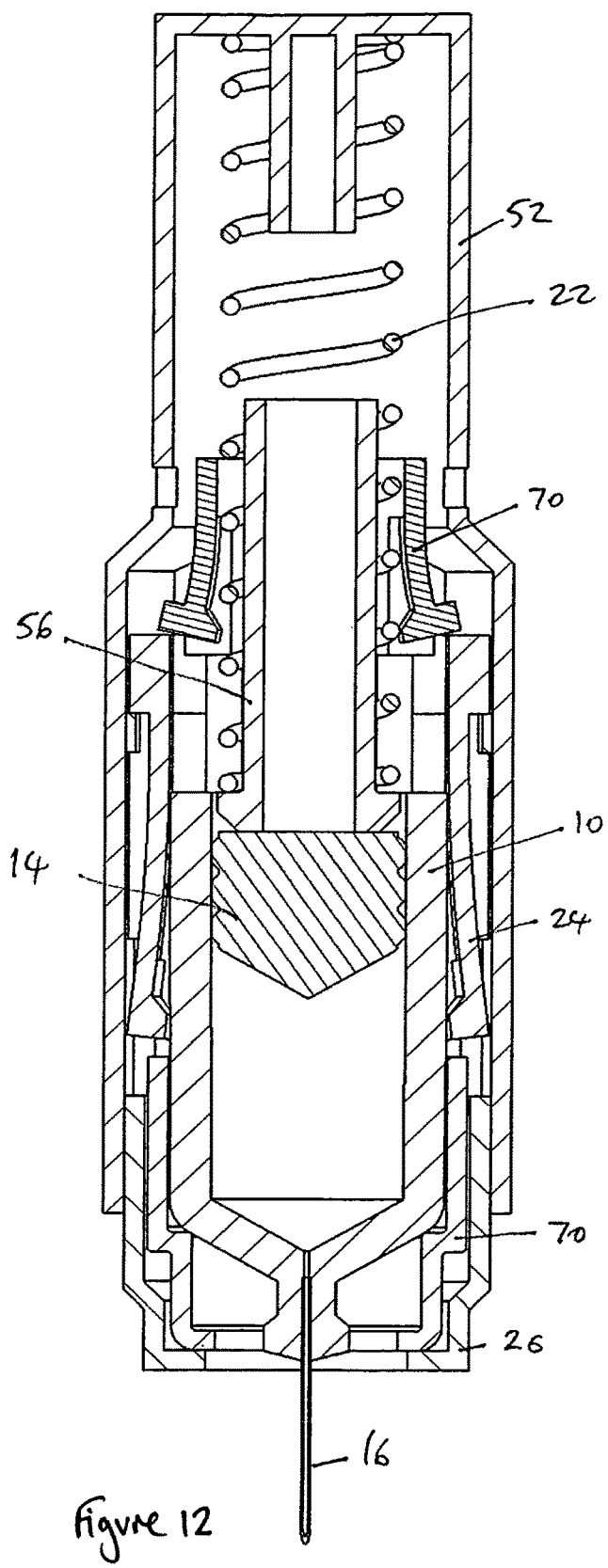
FIG. 12 is a section of the autoinjector of FIG. 1 with the needle in an insertion position.

The force required to move the drug container forward is less that the force required to move the plunger 14 within the drug container 10, and so the drug container is moved first. FIG. 12 shows the autoinjector with drug container 10 in its most forward position, with the needle 16 extending beyond the front end of the skin sensor component 26 into a patient. Further forward movement of the drug container is prevented by the front end housing 70 abutting the front end of the drug container.

Figure 13:
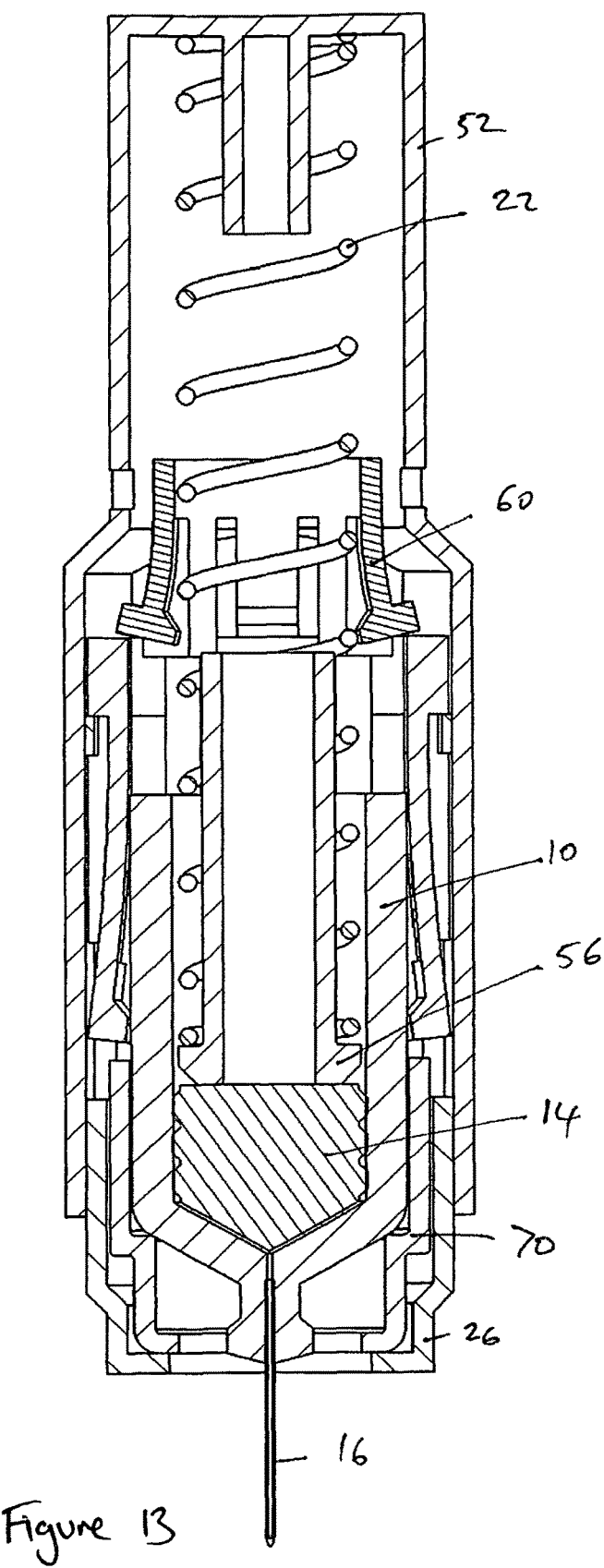
FIG. 13 is a section of the autoinjector of FIG. 1 following delivery of the drug.

The plunger 14 is then moved by the force of the expanding spring 22 through the drug container 10 to expel the drug 12 through the needle 16. FIG. 13 shows the plunger 14 at the front end of the drug container 10 with the drug delivery completed. The spring 22 is then in its most extended position.

Variations to the described embodiment are of course possible, such as the incorporation known elements such as additional needle safety mechanisms and different arrangements for attaching the needle to the drug container. It is also possible to use a differently shaped locking component or a plurality of separate locking components, for example. The locking components may be removed from the autoinjector in an unlocking operation or may be broken in an unlocking operation, or portions of the locking components may be rotated relative to one another or their relative states otherwise altered.

The invention provides a drive mechanism that can be assembled at a first location and delivered in a locked condition to a second location where a drug filling operation is carried out. The drive mechanism can then be assembled to other components to form an autoinjector and the drive mechanism simply unlocked following assembly but prior to delivery to end users. The invention is particularly advantageous for autoinjectors with front end activation, using a skin sensor or equivalent.

The invention claimed is:

1. An autoinjector for use at an injection site, the autoinjector comprising a drive mechanism and a drug containing portion,
    the drive mechanism comprising:
       a housing;
       a drive means coupled to, or forming part of, the housing, the drive means comprising a resilient member;
       a retaining means coupled to, or forming part of the housing, the retaining means engaging the drive means in a first position to retain the drive means in a first deformed condition; and
       a coupling means for coupling with the drug containing portion, wherein the coupling means is a latch, an aperture, or a screw fitting provided on the housing,
       the retaining means releasing the drive means from the first deformed condition when the retaining means is moved to a second position, and the drug containing portion being configured such that the drug containing portion retains the drive means in the second deformed condition when the retaining means is moved the second position until selective release of the drive means from the second deformed condition, wherein the drive means in the second deformed condition is expanded relative to the first deformed condition, wherein the drive means in the second deformed condition stores sufficient potential energy for driving the autoinjector, the autoinjector further comprising a release mechanism configured to selectively release the drive means from the second deformed condition when the autoinjector is to be used.

2. The autoinjector according to claim 1, wherein the retaining means comprises a locking component, the locking component engaging one or more apertures or locking surfaces on the housing in the first position.

3. The autoinjector according to claim 2, wherein the locking component is disengaged from the one or more apertures or locking surfaces on the housing in the second position.

4. The autoinjector according to claim 2, wherein the locking component is stressed in the first position.

5. The autoinjector according to claim 1, wherein the resilient member comprises one or more deformable springs held within the housing.

6. The autoinjector according to claim 1, wherein the drive means comprises a spring engaging component, the spring engaging component coupled to the resilient member and to the retaining means in the first position.

7. The autoinjector according to claim 6, wherein the spring engaging component has a first bearing surface and a locking component has a second bearing surface, wherein, in the first position, the first bearing surface engages the second bearing surface.

8. The autoinjector according to claim 6, wherein the drug containing portion contains a drug to be dispensed and a plunger, wherein the spring engaging component forms a pusher rod configured to engage the plunger during operation of the autoinjector.

9. The autoinjector according to claim 1 wherein the retaining means engages a plurality of apertures in the housing.

10. The autoinjector according to claim 1, wherein the retaining means is connected to the coupling means such that the retaining means cannot move to the second position when the coupling means is not engaged with the drug containing portion.

11. The autoinjector according to claim 1, wherein the release mechanism comprises a movable skin sensor, configured such that when the skin sensor is pressed onto an injection site, the skin sensor moves to release the drive means from the second deformed condition.

12. A method for assembling an autoinjector comprising the steps of:
    placing or forming a resilient drive member in a first housing portion;
    retaining the resilient drive member in the first housing portion in a first deformed condition using a retaining means coupled to the resilient drive member in a first position;
    subsequently coupling the first housing portion to a second housing portion, the second housing portion containing a drug to be dispensed by the autoinjector; and
    moving the retaining means to a second position to release the resilient drive member to a second deformed condition, wherein the second housing portion retains the resilient drive member in the second deformed condition until selective release of the resilient drive member from the second deformed condition when the autoinjector is to be used, and wherein in the second deformed condition the resilient drive member stores sufficient potential energy for needle insertion and/or drug ejection when the autoinjector is to be used, wherein the resilient drive member in the second deformed condition is expanded relative to the first deformed condition.

13. The method according to claim 12, wherein the step of moving the retaining means is performed as a consequence of the step of coupling.

14. The method according to claim 12, wherein the step of moving the retaining means comprises pushing a portion or portions of the retaining means through one or more apertures in the first housing portion.

15. A kit for assembly into an autoinjector, the kit comprising: a drive mechanism, and a drug containing portion,
the drive mechanism comprising:
a housing;
a drive means coupled to, or forming part of, the housing,
the drive means comprising a resilient member;
a retaining means coupled to, or forming part of, the housing, the retaining means engaging the drive means in a first position to retain the drive means in a first deformed condition; and
a coupling means for coupling with the drug containing portion, wherein the coupling means is a latch, an aperture, or a screw fitting provided on the housing;
wherein the retaining means releases the drive means from the first deformed condition when the retaining means is moved to a second position, and
wherein, when the drive means is coupled to the drug containing portion, the drug containing portion retains the drive means in a second deformed condition when the retaining means is moved to the second position until selective release of the drive means from the second deformed condition, wherein the drive means in the second deformed condition is expanded relative to the first deformed condition, wherein the drive means in the second deformed condition stores sufficient potential energy for driving the autoinjector and is releasable from the second deformed condition by a user when the autoinjector is to be used.

16. An autoinjector for use at an injection site, the autoinjector comprising: a drug containing portion; a drive mechanism,
the drive mechanism including
a housing;
a coupling means for coupling with the drug containing portion, wherein the coupling means is a latch, an aperture or a screw fitting provided on the housing;
a drive spring coupled to, or forming part of, the housing, the drive spring being capable of being retained in a first deformed condition and the drive spring being capable of being retained in a second deformed condition, the drive spring being expanded in the second deformed condition relative to the first deformed condition;
a locking component coupled to, or forming part of, the housing, the locking component being capable of moving between a first position and a second position; and
an aperture on the housing, the locking component engaging the aperture when the locking component is in the first position to retain the drive spring in the first deformed condition, and the locking component allowing the drive spring to expand from the first deformed condition to the second deformed condition when the locking component is moved to the second position to disengage the aperture,
the drug containing portion being configured such that the drug containing portion retains the drive spring in the second deformed condition when the locking component is moved to the second position until selective release of the drive spring from the second deformed condition, wherein the drive spring in the second deformed condition stores sufficient potential energy for driving the autoinjector; and
a movable skin sensor, configured such that when the skin sensor is pressed onto an injection site, the skin sensor moves to release the drive spring from the second deformed condition.

* * * * *